(12) United States Patent
Baranton et al.

(10) Patent No.: US 9,585,552 B2
(45) Date of Patent: Mar. 7, 2017

(54) DEVICE AND METHOD FOR MEASURING AT LEAST ONE OBJECTIVE OCULAR REFRACTION CHARACTERISTIC OF A PATIENT FOR A PLURALITY OF VISUAL RANGES

(71) Applicant: ESSILOR INTERNATIONAL (COMPAGNIE GENERALE D'OPTIQUE), Charenton-le-Pont (FR)

(72) Inventors: Konogan Baranton, Charenton-le-Pont (FR); Benjamin Rousseau, Charenton-le-Pont (FR); Fabien Divo, Charenton-le-Pont (FR); Guilhem Escalier, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 1 day.

(21) Appl. No.: 14/411,933

(22) PCT Filed: Jul. 4, 2013

(86) PCT No.: PCT/FR2013/051596
§ 371 (c)(1),
(2) Date: Dec. 30, 2014

(87) PCT Pub. No.: WO2014/006342
PCT Pub. Date: Jan. 9, 2014

(65) Prior Publication Data
US 2015/0374224 A1    Dec. 31, 2015

(30) Foreign Application Priority Data

Jul. 6, 2012  (FR) ...................... 12 01926

(51) Int. Cl.
*A61B 3/00* (2006.01)
*A61B 3/09* (2006.01)
(Continued)

(52) U.S. Cl.
CPC .............. *A61B 3/0091* (2013.01); *A61B 3/00* (2013.01); *A61B 3/08* (2013.01); *A61B 3/085* (2013.01);
(Continued)

(58) Field of Classification Search
CPC ......... A61B 3/0091; A61B 3/103; A61B 3/00; A61B 3/08; A61B 3/085; A61B 3/09; G02C 13/005
(Continued)

(56) References Cited

U.S. PATENT DOCUMENTS 4,881,806 A  * 11/1989  Bovet ................. A61B 3/111
                                                  351/204
6,257,721 B1 * 7/2001  Hayashi ............. A61B 3/112
                                                  351/204
(Continued)

FOREIGN PATENT DOCUMENTS

| EP | 0305238 A1 | 3/1989 |
| FR | 2914173 A1 | 10/2008 |
| FR | 2952517 A1 | 5/2011 |

OTHER PUBLICATIONS

International Search Report, dated Nov. 14, 2013, from corresponding PCT application.
(Continued)

*Primary Examiner* — Bumsuk Won
*Assistant Examiner* — William R Alexander
(74) *Attorney, Agent, or Firm* — Young & Thompson (57) ABSTRACT

A device for measuring the objective ocular refraction of a patient for a plurality of visual ranges, which includes a
(Continued)

variable proximity optical sight system capable of selectively generating a first target and a second target and an image-capturing device having an optical measurement axis intended for being aligned with a line of sight of the patient, the image-capturing device being capable of capturing a first ocular refraction image when the first target is activated and a second ocular refraction image when the second target is activated. The image-capturing device and the optical sight system are arranged such that the optical measurement axis and the optical sight axis are arranged such that the optical measurement axis and the optical sight axis are contained in a single plane and the optical measurement axis is tilted at an angle alpha between +5 degrees and +85 degrees relative to the horizontal.

17 Claims, 4 Drawing Sheets (51) Int. Cl.
*A61B 3/08* (2006.01)
*A61B 3/103* (2006.01)
*G02C 13/00* (2006.01)

(52) U.S. Cl.
CPC ............... *A61B 3/09* (2013.01); *A61B 3/103* (2013.01); *G02C 13/005* (2013.01)

(58) Field of Classification Search
USPC .................................. 351/200, 205, 206, 211
See application file for complete search history.

(56) References Cited

U.S. PATENT DOCUMENTS

| | | | |
|---|---|---|---|
| 8,360,580 | B2 | 1/2013 | Chauveau |
| 8,708,490 | B2 | 4/2014 | Baranton et al. |
| 2003/0108350 | A1 | 6/2003 | Brauning |
| 2004/0218142 | A1* | 11/2004 | Wakil ................... A61B 3/0091 351/205 |
| 2006/0244911 | A1 | 11/2006 | Shimizu et al. |
| 2007/0200927 | A1* | 8/2007 | Krenik ................... A61B 3/032 348/47 |
| 2009/0303435 | A1* | 12/2009 | Flitcroft ................. A61B 3/113 351/202 |
| 2010/0128220 | A1* | 5/2010 | Chauveau ............... A61B 3/111 351/204 |
| 2010/0195045 | A1* | 8/2010 | Nauche ................. G02C 13/005 351/204 |
| 2011/0292054 | A1* | 12/2011 | Boker ..................... G06T 9/001 345/473 |
| 2012/0033178 | A1* | 2/2012 | Chauveau ............ G02C 13/005 351/204 |
| 2012/0154751 | A1* | 6/2012 | Pelah ................... A61B 3/0041 351/224 |
| 2015/0109578 | A1* | 4/2015 | Baranton ............. A61B 3/0075 351/205 |
| 2015/0208919 | A1* | 7/2015 | Pohjanen ............... A61B 3/156 351/208 |

OTHER PUBLICATIONS

Kusel, "Light Intensity Distribution in Eccentric Photorefraction Crescents", J. Opt. Soc. Am. A/ vol. 15, No. 6 (Jun. 1998).

* cited by examiner

DEVICE AND METHOD FOR MEASURING AT LEAST ONE OBJECTIVE OCULAR REFRACTION CHARACTERISTIC OF A PATIENT FOR A PLURALITY OF VISUAL RANGES

TECHNICAL FIELD OF THE INVENTION

Generally, the present invention relates to the field of apparatuses and methods for measuring the ocular refraction of a subject. It more particularly relates to an apparatus and method for measuring ocular refraction in one or more visual attitudes of a subject, for example in a far-vision (FV) and/or near-vision (NV) attitude, the head of the subject not being physically restrained. Opticians, ophthalmologists and optometrists are the main users of the invention.

PRIOR ART

Precise determination of the ocular refraction parameters of an individual in various cephalic postures and/or for various visual attitudes is essential if vision correcting spectacles appropriate for these various postures and/or visual attitudes are to be manufactured.

Various apparatuses and methods for measuring ocular refraction are known that allow the objective ocular refraction of a wearer to be measured for various visual attitudes and/or cephalic postures. These apparatuses are based on various techniques, for example photorefraction, or on the retinoscopy technique. In particular, it is known to use an automatic refractometer, an aberrometer, a retinoscope or a photorefraction apparatus in order to measure the objective refraction of the eyes of an individual in at least one visual attitude.

An automatic refractometer may allow, under particular conditions, the refraction of the wearer to be measured for far vision, for example through a transparent window allowing him to see straight ahead, but also for near vision as stimulated by a target generated by the apparatus. Such an apparatus requires a chin rest and adjustment both of the chin rest and the measuring head of the apparatus. However, automatic refractometer measurements are limited to a cephalic posture constrained by the chin rest and to a generally horizontal angle of vision. Automatic refractometers do not allow refraction to be measured for all visual attitudes, in particular for different head positions. In addition, automatic refractometers are bulky. An automatic refractometer generally allows certain parameters such as pupillary distances (PD) to be measured. However, automatic refractometers do not allow other essential fitting parameters such as half-distances, height (H) or pantoscopic angle, the eye/glass distance (EGD) or even the position of the center of rotation of the eye (CRE) to be measured.

Refractometry apparatuses generally place constraints on the spectacle wearer by way of chin rests, forehead rests or by requiring the wearer to direct his gaze toward a target in an apparatus or even to close one eye. These postural and/or visual constraints do not allow ocular refraction measurements to be carried out under conditions that are representative of natural binocular vision. In addition, these apparatuses do not allow the ocular refraction of the subject to be measured while his head is in different positions that are representative of different types of visual attitude, such as a far-vision attitude with the gaze directed straight ahead and the vision attitude adopted when reading close-up with the gaze lowered.

However, ocular refraction characteristics vary, especially depending on posture; on far-vision, near-vision and intermediate-vision conditions; and on monocular or binocular gaze direction.

More mobile apparatuses, such as retinoscopes or photorefraction apparatuses, also exist. These apparatuses do not require a chin rest and allow the future spectacle wearer to adopt a natural attitude and any posture. Nevertheless, these apparatuses require, on the part of the optician, a certain dexterity if he is to be able to measure the ocular refraction parameters of the wearer for different postures. Specifically, for a given head position the apparatus must be practically aligned with the visual axis. Lastly, these apparatuses are not suitable for measuring fitting parameters (PD/H/EGD/CRE).

Measurement of all the parameters required to fit correcting lenses in a spectacle frame for a wearer requires another measuring apparatus and additional measuring steps. The length of time required to perform all of the ocular refraction measurements and fitting-parameter measurements decreases the effectiveness of the overall measurement of the wearer and the precision of the measurement, the measurement conditions possibly being different between the refraction measurement and the measurement of the fitting parameters. Furthermore, using two different apparatuses is more time-consuming, more complex and requires more skill on the part of the operator. In practice, using two apparatuses is inescapably more expensive.

SUBJECT OF THE INVENTION

One of the aims of the present invention is to provide a device and a method for precisely, rapidly and reliably measuring objective ocular refraction characteristics for an individual under various set vision conditions, for example far-vision (FV) and near-vision (NV) conditions, while the individual is in an unconstrained posture. Another aim of the invention is to provide a device and method allowing the measurement of objective ocular refraction and the measurement of fitting parameters to be combined, so that these two types of measurement can be carried out on the individual under the same vision and posture conditions.

In order to remedy the aforementioned drawbacks of the prior art, the present invention provides a binocular device for measuring at least one objective ocular refraction characteristic of a subject for a plurality of vision distances. More particularly, according to the invention said device comprises:

an optical system for generating a focus of variable proximity, able to generate selectively a first target having a first proximity value P1 and at least one second target having a second proximity value P2, said first target and said second target being centered on one and the same focus optical axis;

at least one light source able to generate at least one illuminating beam in the direction of the two eyes of the subject;

an image-capturing apparatus, said apparatus having a measurement optical axis aligned with a gaze axis of the subject, said apparatus being suitable for receiving an ocular refraction beam by refraction of the at least one illuminating beam in the eyes of the subject, the image-capturing apparatus being suitable for capturing a first ocular refraction image of the two eyes when the first target of proximity P1 is activated and at least one second ocular refraction image of the two eyes when the second target of proximity P2 is activated; and a processor suitable for receiving the first ocular refraction image and the second ocular refraction image in order to deduce therefrom a measurement of at least one objective ocular refraction characteristic of the two eyes of the subject depending on the first proximity value P1 and the second proximity value P2, a case holding the focus-generating optical system, the at least one light source and the image-capturing apparatus;

the focus optical axis is inclined at an angle alpha to the horizontal, the angle alpha being comprised between +5 degrees and +85 degrees when the case is placed on a horizontal surface, the image-capturing apparatus and the processor being suitable for measuring pupillary distances for the first proximity value P1 and for the second proximity value P2 and/or at least one fitting parameter among height, pantoscopic angle, eye/glass distance and the position of the center of rotation of the eye.

The device of the invention allows refraction measurements to be carried out for a plurality of vision distances in at least one vision posture in which the gaze of the subject is inclined relative to a horizontal line. The device of the invention especially permits a near-vision refraction measurement in an unconstrained natural vision posture. The device of the invention allows the proximity value of the target to be varied and the refraction to be measured for another proximity value without modifying the focus axis, which remains inclined relative to a horizontal line.

Preferably, the angle alpha is comprised between +15 degrees and +40 degrees.

Advantageously, the measuring device comprises means for moving and/or orienting the focus optical axis so as to align the measurement optical axis with the axis of the gaze of the subject.

According to one particular embodiment, the device furthermore comprises means for measuring the distance between said device and the head of the subject, said means for measuring distance being chosen from: a telemeter, an image-processing system based on image quality, an image-processing system based on the measurement of reference marks mounted on a clip fastened to a spectacle frame, a gauging system or a system for measuring distance by ultrasound.

Advantageously, the at least one light source comprises at least one infrared source and the image-capturing apparatus is able to capture images in the infrared.

According to one particular embodiment, the device furthermore comprises an optical beam splitter placed on the optical path between the subject and the at least one source, the image-capturing apparatus, the optical beam splitter being able to combine the illuminating beam and the first target or the second target on the focus optical axis in the direction of the eyes of the subject, said beam splitter being able to direct the ocular refraction beam toward the image-capturing apparatus on the measurement optical axis.

Advantageously, the optical beam splitter comprises a dichroic mirror.

Preferably, the optical beam splitter comprises a dichroic mirror able to transmit the infrared illuminating beam and reflect the target beam.

Advantageously, the angle between the measurement optical axis and the focus optical axis is smaller than 10 degrees.

Preferably, the measurement optical axis and the focus optical axis are coincident.

According to one particular embodiment, the image-capturing apparatus is suitable for forming an image of the face of the subject on an object field having a diameter of at least 50 mm.

The invention also relates to a binocular method for measuring at least one objective ocular refraction characteristic of a subject for a plurality of vision distances, said method comprising the following steps:

generating a first target having a first proximity value P1 along a focus optical axis aligned with the axis of the gaze of the subject, the axis of the gaze being inclined at an angle alpha1 comprised between +5 degrees and +85 degrees to the horizontal;

capturing a first ocular refraction image of the two eyes in a measurement direction when the first target of proximity P1 is activated;

generating a second target having a second proximity value P2 along the same focus optical axis, said axis being intended to be aligned with the axis of the gaze of the subject, the axis of the gaze being inclined at an angle alpha2 comprised between +5 degrees and +85 degrees to the horizontal;

capturing at least one second ocular refraction image of the two eyes in the same measurement direction when the second target of proximity P2 is activated; and digitally processing the first ocular refraction image and the at least one second ocular refractive image in order to deduce therefrom at least one objective ocular refraction characteristic of the two eyes of the subject depending on the first proximity value P1 and the second proximity value P2, the method furthermore comprising a step of measuring pupillary distances for the first proximity value P1 and for the second proximity value P2 and/or at least one fitting parameter among height, pantoscopic angle, eye/glass distance and the position of the center of rotation of the eye.

According to a preferred aspect of the method of the invention, a first ocular refraction image is captured for a first posture of the subject, a second ocular refraction image is captured for a second posture of the subject different from the first posture, and the image-capturing steps are carried out under conditions where the head of the subject is free from external physical constraints.

In one particular embodiment, the method furthermore comprises a preliminary placing step so as to position and orient the measuring device relative to the subject.

Advantageously, the measuring method comprises an alerting step in the case of relative mispositioning or relative misorientation of the measuring device and the subject.

DETAILED DESCRIPTION OF AN EXAMPLE EMBODIMENT

The following description, given with regard to the appended drawings, which are given by way of nonlimiting example, will allow what the invention consists of and how it can be carried out to be understood.

DEVICE

A device is provided allowing ocular refraction measurements to be performed without constraining the head of the wearer, i.e. without a chin rest or forehead rest. Therefore, the device leaves the wearer free to choose his head position. The device allows objective ocular refraction measurements to be obtained for different vision attitudes, including different cephalic postures. Optionally, the device of the invention also allows fitting parameters to be measured. The device is both compact and simple to use.

Figure 1:
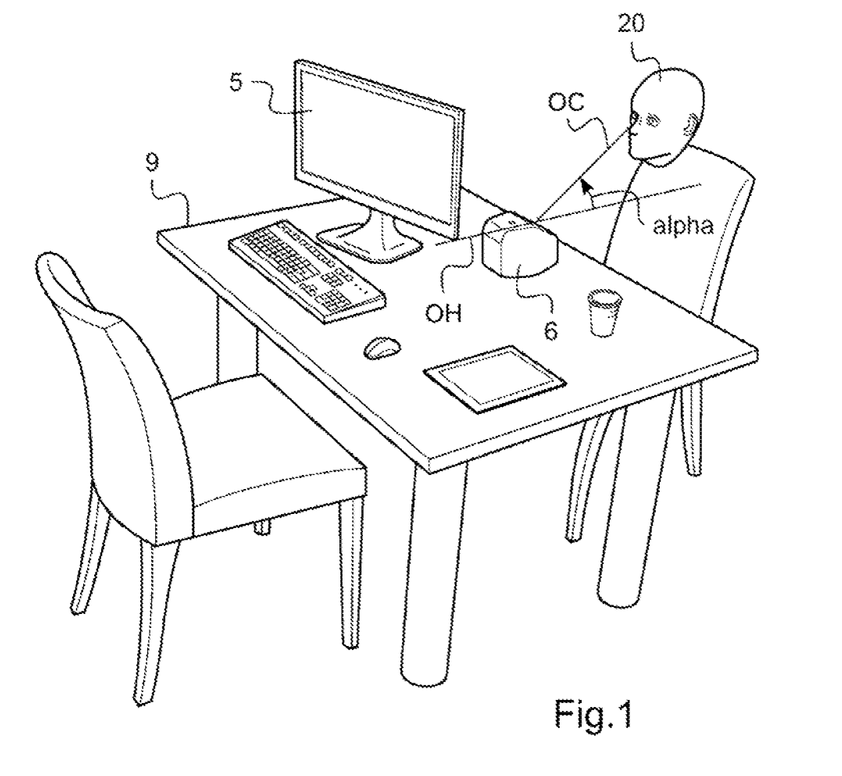
FIG. 1 schematically shows a measuring apparatus according to one embodiment of the invention, placed on a desk facing a wearer.

FIG. 1 schematically shows a device according to a first embodiment of the invention, under operating conditions where the device is placed on a desk facing a seated wearer. The device in FIG. 1 comprises:

a case 6 that incorporates an image sensor (for example a video camera), an illuminating system for illuminating the face 20 of the wearer (especially his two eyes) and an optical system for generating a focus of variable proximity that can be set to at least two different proximity values, for example to a far-vision value and to a near-vision value;

a processor allowing the refraction values of the wearer and optionally fitting-parameter measurements to be extracted from the images taken by the video camera; and a system for controlling the measurement and display of the measurement results.

Advantageously, a computer equipped with a graphical interface, for example a display screen 5, performs the functions of the processor and of the system for controlling and displaying the measurement results.

The case 6 and the display screen 5 are placed on a desk 9. The case 6 is placed facing the face 20 of the wearer so as to allow the face 20 of the wearer to be illuminated and images of at least one portion of the face of the wearer, and in particular of his two eyes, to be acquired. Advantageously, the image sensor comprises a video camera, preferably functioning in the infrared. The video camera films the future spectacle wearer. More precisely, the video camera is pointed toward the face 20 of the wearer at a distance comprised between 300 and 700 mm, the image being focused using the face of the wearer. Advantageously, the field of the video camera allows both the eyes of the wearer and a large portion of his face, especially around the eyes, to be displayed.

If the wearer is equipped with a spectacle frame 7 (his frame with correction or a selected frame), the field of the video camera allows most and preferably all of this frame to be seen.

If the wearer is equipped with a frame with a clip 8 equipped with reference marks 18, 28, 38 (see FIG. 4) or a special frame equipped with reference marks, these reference marks can be seen by the video camera, i.e. the field of the video camera is compatible with the position of the reference marks relative to the eyes, and the reference marks possess a sufficient contrast in the infrared to be able to be detected automatically.

Figure 2A:
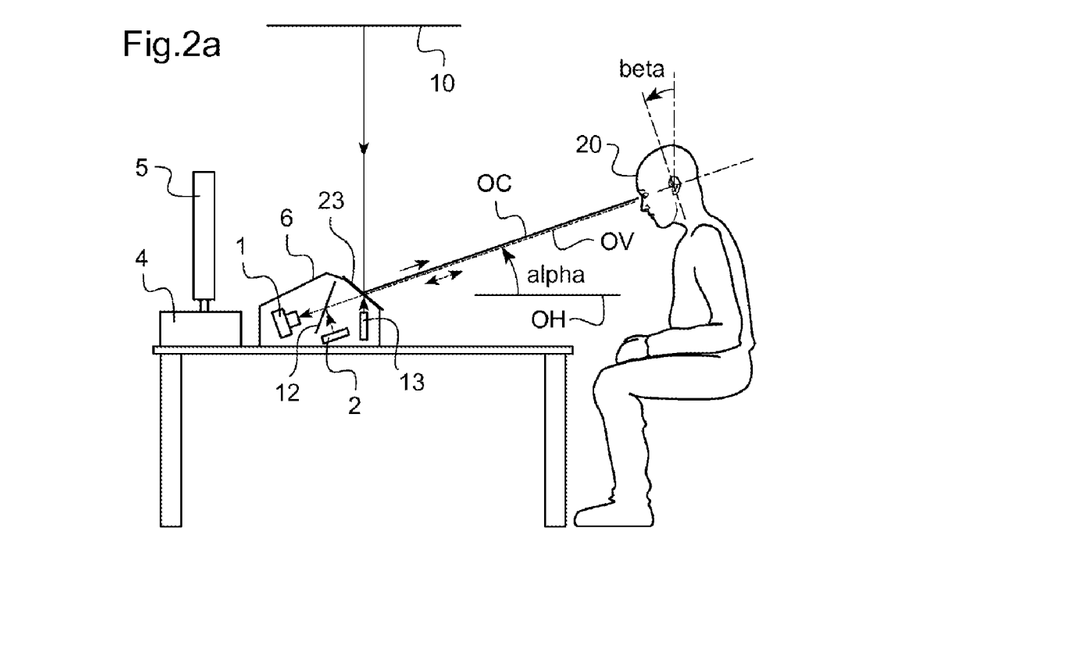
FIG. 2a is a side view of a measuring apparatus according to one embodiment of the invention, for a far-vision attitude.
Figure 2B:
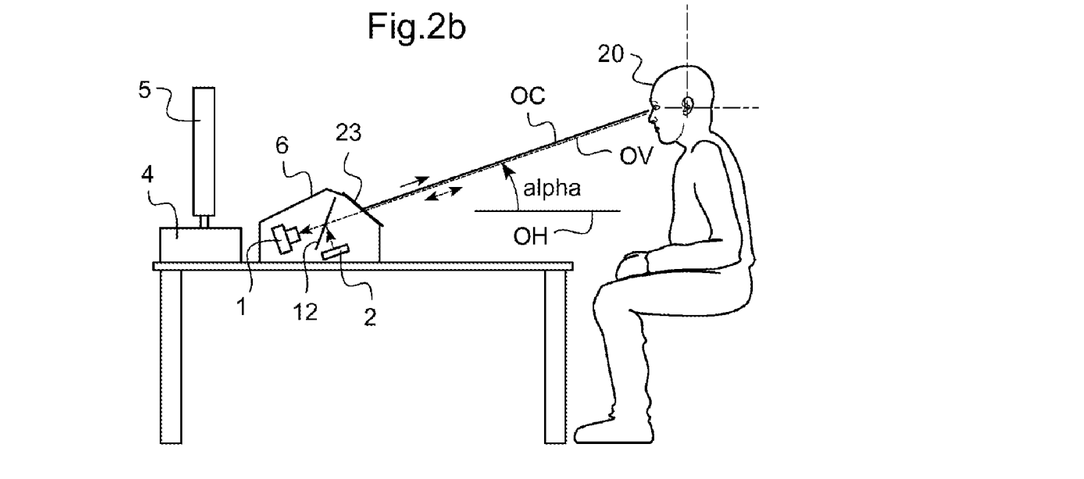
FIG. 2b is a side view of the measuring apparatus in FIG. 2a, for a near-vision attitude.

The video camera films the wearer with a certain non-zero angle alpha relative to the horizontal. Preferably, the device is positioned on a desk 9, for example a dispensing desk of the optician, the desktop being at a height lower than that of the face 20 of the wearer. The line of sight of the video camera is thus inclined by a positive angle alpha (see FIGS. 1 and 2).

FIGS. 2a and 2b show a cross-sectional view of the device including the case 6 of the device in FIG. 1.

The case 6 in FIGS. 2a-2b comprises:

a video camera 1, preferably with an infrared image sensor, allowing the face of the wearer to be filmed; the optical axis OC of the video camera 1 is placed so as to target the axis of the gaze of the wearer; the optical axis OC forms a positive angle alpha to a horizontal straight line OH;

an illuminating system 2, preferably an infrared illuminating system, used to illuminate the eyes of the wearer and to carry out the refraction measurements by retinoscopy or photorefraction;

a beam splitter 12 placed on the optical path between the video camera 1 and the illuminating system 2 in order to combine the illuminating beam on the optical axis of the video camera;

an optical focus-generating system making it possible to get the wearer to switch from viewing a preset distance to viewing another different distance while maintaining the same gaze direction; and a computer 4 equipped with a display screen 5, for controlling the activation of the elements in the case and displaying the measurement results, preferably in graphical form.

In FIGS. 2a and 2b dotted lines show the optical paths of infrared beams and solid lines the optical paths of beams in the visible domain. The beam splitter 12 is oriented so as to direct the infrared illuminating beam generated by the illuminating system 2 toward an aperture in the case 6 in the direction of the face 20 of the wearer. By reflection from the face and eyes of the wearer, an infrared beam is returned in the direction of the case. The beam splitter 12 receives the back-reflected infrared beam and transmits it in the direction of the video camera 1. The video camera 1, the illuminating system 2 and the beam splitter 12 are placed relative to one another so that the optical axis OC of the video camera 1 makes an angle alpha to a horizontal line OH, and so that the illuminating beam generated by the illuminating system is centered on the optical axis OC.

Particularly advantageously, the optical axis OC of the image sensor is coincident with the optical axis of the illuminating beam. The optical axis OC is directed toward the face of the wearer so that, the wearer having an unconstrained vision posture, the axis of his gaze is preferably centered on the optical axis OC.

The measuring device furthermore comprises, in front of the video camera and the illuminating system, an optical focus-generating system allowing the observation proximity seen by the wearer to be varied, typically between −0.5 and +10 diopters.

Preferably, as shown in FIG. 2a, to stimulate far vision a particular planar mirror 23 called a cold mirror is used. This mirror 23 has the particularity of being transparent in the infrared and reflective in the visible. The video camera 1 acquires images through the mirror 23 as though through a transparent window. The mirror 23 may be used conjointly with a light source 13 emitting radiation in the visible (for example in the green) in order to present the wearer with a distant image to focus on. Alternatively, the mirror 23 may be used without a source 13. By way of illustration, the mirror 23 may be oriented so that the wearer sees the ceiling 10 of the opticians. When the source 13 is present and turned on, the latter generates, on the ceiling 10, a luminous pattern that the wearer may see in reflection in the mirror 23. The ceiling zone intended to be illuminated by the source 13 will preferably be free of lighting and possess a scattering surface.

In FIG. 2a, when the source 13 is turned off, the wearer regards the ceiling 10 directly. The wearer thus observes a scene under proximity conditions of close to 0 diopters. As an alternative, to ensure the wearer observes under far-vision conditions, the mirror 23 may be inclined such that the wearer observes an object actually located at a far-vision distance (an object outside the opticians for example), the axis of his gaze being aligned with the optical axis OC of the video camera. The head of the wearer is inclined by an angle beta relative to the vertical so as to simulate the far-vision posture in which the axis of the gaze points straight ahead. Under these conditions, the video camera makes it possible to simultaneously film the face of the wearer and measure far-vision refraction.

Alternatively, a translationally movable mirror may be used to switch from a far-vision target to a near-vision target.

According to one particular embodiment, shown in FIG. 2b, the mirror 23 bears a screen-printed print on its surface in order to provide a pattern stimulating near vision (at about 400 mm from the face of the wearer). Thus, to perform the near-vision refraction measurement the source 13 (if it is present) is turned off and the wearer is asked to look at the screen-printed pattern on the surface of the mirror 23. The head of the wearer is here upright and the axis of the gaze is inclined relative to a horizontal line so as to simulate the near-vision posture adopted with progressive glasses. Under these conditions, the video camera makes it possible to simultaneously film the face of the wearer and measure near-vision refraction.

Alternatively, for the far-vision distance, a concave cold mirror may be used the focal point of which corresponds to a distance of about 400 mm (the focal point coincides with the face of the wearer). In this case, the face of the wearer, which is focused at infinity by the concave cold mirror, is used directly for the far-vision measurement. For the near-vision measurement, the mirror is for example switched in order to allow another target to be observed.

Alternatively, for the near-vision measurement, one of the following may be used: a light source placed near the mirror and near the axis of the video camera; a screen-printed mask that is opaque in the visible and transparent in the IR, this mask being superposed on the mirror (the wearer is thus not bothered by the reflection in the mirror when focusing in the near field); or a drilled mask, the hole serving as a near-vision focal point.

The screen-printed prints may be produced with inks that are transparent in the infrared or fluorescent in the visible in order not to affect the measurement.

Figure 3:
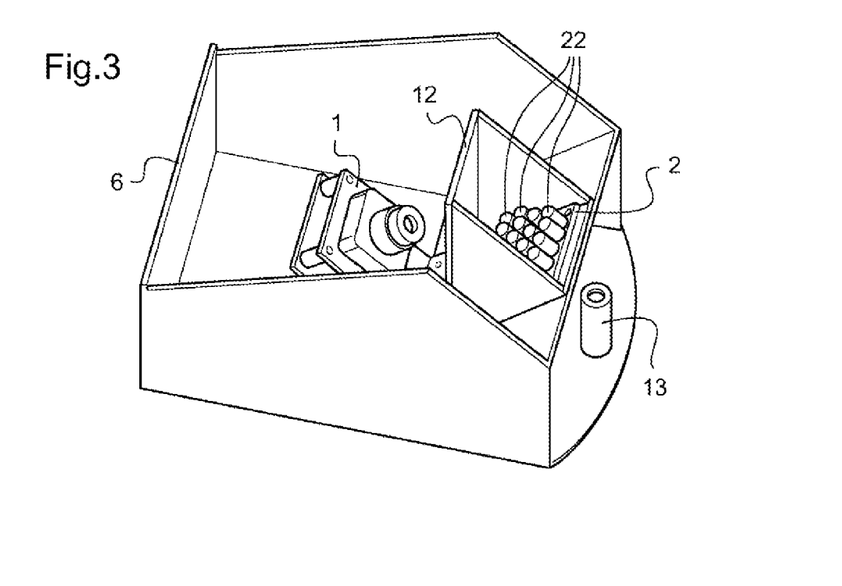
FIG. 3 is a perspective view of a measurement case of a measuring apparatus according to one embodiment of the invention.

FIG. 3 shows a perspective view of a case of a measuring apparatus according to one embodiment of the invention. FIG. 3 shows details of the illuminating system and the image sensor.

The preferably infrared illuminating system 2 is used to perform photorefraction measurements. Advantageously, the illuminating system comprises a plurality of sectors of infrared light-emitting diodes (LEDs). The LEDs 22 illuminate the face of the wearer and generate, on the retina of each eye of the wearer, a spot the size of which depends on the ametropia of the wearer.

The video camera 1 allows the light intensity associated with scattering of the spot from the retina to be displayed, an intensity gradient related to the ametropia of the eyes then being discernible on the pupil of each eye (well-known principle of photorefraction).

The use of various sectors of LEDs 22 allows the ametropia of the eyes to be measured for different axes and to deduce therefrom sphere/cylinder ametropia parameters.

The various sectors of LEDs are alternately turned on and synchronously images are taken when a particular sector is turned on in order to obtain the refraction measurement for this axis. In the case where the wearer has an astigmatism, variable intensity gradients are observed across the pupils of the eyes.

The various sectors of LEDs 22 form a pattern the center of which coincides with the optical axis OC of the infrared video camera 1. In FIGS. 2a-2b and 3 a plate 12 that is semi-transparent in the infrared is used to achieve this coincidence. Alternatively, the LEDs 22 may also be placed all the way around the objective of the video camera 1.

A processor, represented in FIGS. 1 and 2a-2b by a computer 4, stores the various images and extracts therefrom (by measuring the intensity gradient in the pupils of the eyes depending on the source used) ametropia values for each of the two eyes and for a particular vision condition and visual attitude.

The screen 5 of the computer 6 is used to display the results of measurement. The screen 5 also makes it possible to control the measurement and in particular to ensure that the eyes and face are indeed in the field of measurement of the video camera.

The optician may move the measuring device and orient it (case of a tall/short wearer) in order to place the face and eyes in the measurement field. All that is required to do this is to move and/or orient the case 6.

Advantageously, the case 6 is equipped with sliders in order to make it easy for the optician to move it over the desk 9. It is optionally equipped with a means for adjusting its orientation in order to allow the face of a very tall or very short wearer to be viewed.

Optionally (FIG. 4) the device comprises a clip 8 intended to be placed on the spectacle frame 7 of the wearer. The clip 8 is mounted on the frame 7 of the wearer (selected frame or current frame) or optionally on a special frame used only for the measurement. This clip 8 allows the distance between the wearer and the device to be precisely determined, refraction to be precisely measured and fitting parameters (PD/H/EGD, etc.) to be deduced if it is used with a selected frame. The clip 8 is used to obtain measurements of fitting parameters and/or to allow the head position of the wearer to be precisely controlled and to increase the precision of the refraction measurements.

Figure 4:
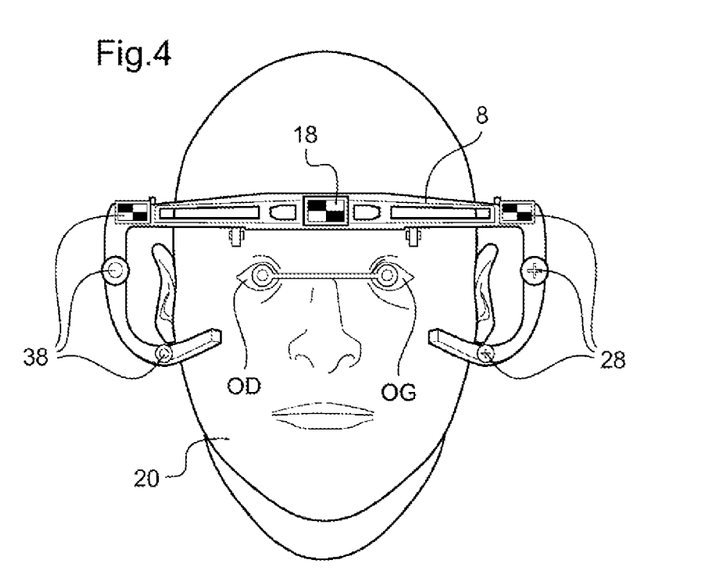
FIG. 4 is an image of a wearer equipped with a clip with reference marks.

As an alternative to the clip 8 any system allowing the position of the head of the wearer relative to the measuring apparatus to be measured may be used (for example: this distance is measured using an optical or ultrasonic telemeter). The position of the head of the wearer may be measured using the frame as a reference, the geometrical parameters of the frame moreover being perfectly known.

As an alternative to a case 6 placed on a desk 9, the device of the invention may be portable (a tablet PC for example), the device comprising an apparatus held in the hand of the wearer himself. Advantageously, the NV measurement is carried out with the apparatus placed on a desk and the FV measurement is carried out with the apparatus held in hand. However, there is a risk with this solution of measurement precision being lost due to the camera moving during the measurement (camera shake).

Figure 5:
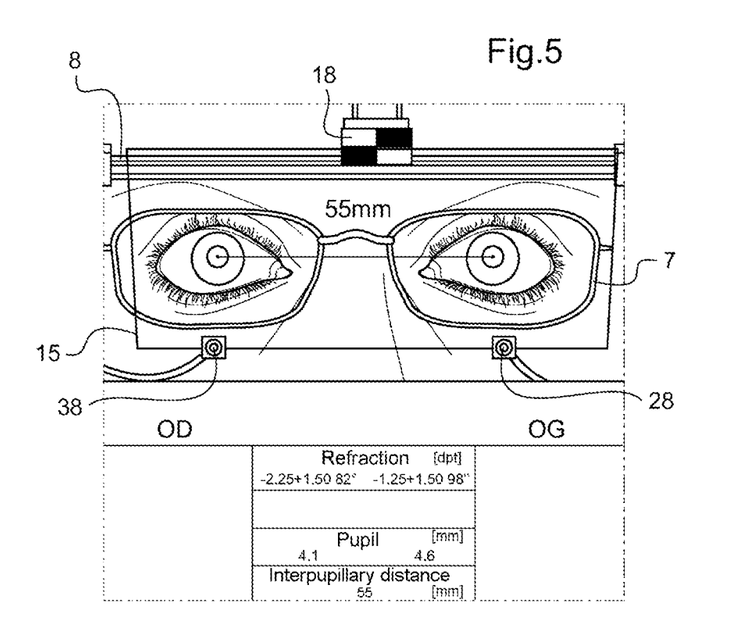
FIG. 5 shows an example graphical interface of a measuring apparatus according to one embodiment of the invention.

FIG. 5 shows an example graphical interface of a measuring apparatus according to one embodiment of the invention after correct adjustment in step 2 of the method, the upper portion shows an image of the face of the wearer, on which image ocular refraction measurement parameters and fitting parameters are displayed, the lower part of the image indicating other wearer ocular refraction parameter measurements and fitting parameters. The video image in the upper portion contains a framing rectangle 15 that is displayed superposed on the image of the face of the wearer. This rectangle 15 is used as a reference to center the eyes of the wearer relative to the field of vision of the video camera.

The advantages of this device are as follows:
it is compatible with desktop use as it is very compact;
it does not place constraints on the wearer (no chin rest or forehead rest);
it is able to measure refraction for at least two proximity values and any cephalic posture;
it is capable of measuring fitting parameters at the same time (via the use of a clip); and
it is able to obtain a more precise refraction measurement (if a clip is used).

Method

A method for measuring refraction for different visual attitudes/postures is also provided, this method comprising the following steps:
measuring refraction for a first preset vision distance and in a first preset posture. The posture of the wearer is controlled via the screen display or optionally using the clip. For example, the axis of the gaze of the wearer is substantially lowered and the proximity of the first vision distance corresponds to the near-vision proximity (FIG. 2b); and
measuring refraction for a second vision distance different from the first vision distance, in a second cephalic posture different from the first cephalic posture. Here again, the new posture is controlled via the screen display or optionally using the clip. For example, the head of the wearer is inclined forward (FIG. 2a). During this second measurement, the gaze axis is substantially identical to that of the first measurement, but the cephalic posture and/or vision distance are different.

Advantageously, the device with regard to FIGS. 2a-2b is used in the following way:

The device is placed on the dispensation desk of the optician. The device is connected to a computer that serves both as a processor and as a graphical interface, display and control system. The optician sits facing the computer and the wearer sits facing the optician. It is assumed here that the wearer is equipped with the selected frame, itself equipped with a clip.

Step 1: Adjusting the Position of the Device

The optician turns on the device and a video image appears on the screen of the computer, displaying the image captured by the infrared (IR) video camera. In order to obtain an image that is bright enough, all of the IR LEDs may be turned on at this point.

The optician then asks the wearer to look at a first target generated by the device (for example the projection onto the ceiling of the source 13 through the mirror 23). The optician then adjusts the device so that the eyes and face of the wearer are located in the field of the video camera by moving the case 6 over the desk.

Optionally, if the wearer is of a height substantially different from average (very short or very tall), the optician may need to adjust the angle alpha in order to center the face of the wearer in the field of the video camera. Alternatively, the height of the wearer may be adjusted (adjustable chair) in order to position the face of the wearer in the field of the video camera.

It may also prove to be necessary to adjust the distance between the video camera and the face of the wearer. In this case, the optician adjusts the distance so as to obtain a clear image on the screen. If the clip 8 is used, the reference marks on the clip may also be used to precisely determine this distance and to indicate to the optician the direction of the adjustment to be made. During this adjusting step, the head of the wearer remains free to move unconstrainedly.

The steps that follow are described in an order that may be changed.

Step 2: Adjusting Far-Vision Head Position

Here, the wearer focuses on the first far-vision target, for example the target projected onto the ceiling by the source 13. The optician may optionally ask the wearer to pivot his head forward or backward while continuing to focus on the target if the optician considers the head of the wearer to be inclined by too much or if he would like to modify the position of the head of the wearer.

For example, if the pupils of the eyes are not centered in the frames, the optician may ask the wearer to incline his head in order to recenter them. This makes it possible to ensure that a posture representative of a far-vision posture is adopted.

Alternatively, the indication of pantoscopic angle provided by the reference marks on the clip may be used to control the head position of the wearer, it for example being verified that the pantoscopic angle measured is close to the pantoscopic angle of the frame.

Generally, the optician may ask the wearer to adopt a head position that he judges to be suitable for the refraction measurement.

Once the apparatus has been correctly positioned, an image equivalent to that shown in FIG. 5 is displayed on the screen. Here, the head position of the wearer is such that his gaze is lowered by almost zero relative to his head (similar to the lowering of the gaze relative to the head for far vision).

A measurement may then be taken, and the various sectors of IR LEDs are turned on in a preset sequence in order to carry out a first refraction measurement. The refraction value of each eye is then displayed at the bottom of the display screen, such as shown in FIG. 5, for a first posture and for the first vision distance, or in other words for the first proximity value P1.

It may be checked that the wearer is indeed looking at the target on the ceiling 10 by verifying that his gaze converges on the target on the ceiling, for example by measuring the relative positions of the pupils and corneal reflections.

In practice, to take a measurement the following procedure is used:

When the wearer is considered to be correctly positioned, the measurement is triggered (for example by pressing on a button) and a sequence of images taken with the various IR LEDs is obtained.

The sequence of images is stored in the computer 4 for subsequent processing.

One of these images may for example be taken with all the IR LEDs turned on, thereby maximizing light flux. In this image, the position of the pupils, the position of the corneal reflections and the position of the various markers on the clip are identified.

The position of the corneal reflections or of the centers of the pupils allows the interpupillary distance (PD) to be determined in number of image pixels, and the distance in pixels between the markers on the clip allows the size of one pixel in mm to be determined. It is thus possible to calculate the pupillary-distance value in mm.

Likewise, it is possible to measure the distance between the corneal reflections/centers of the pupils and the lower edges of the frame in order to determine fitting heights, or the distance between the corneal reflection/centers of the pupils and the middle of the bridge in order to determine the ½ pupillary distances.

The other images of the sequence may be used to measure refraction, each image for example being taken when only one sector of IR LEDs is turned on, and therefore providing an ametropia measurement for various axes.

The size of the pupil and its intensity or more precisely its intensity gradient are determined in each image. The direction of the gradient and its magnitude characterize directly the ametropia of the eye in question on the axis measured, and all that is required is at least three images for three different sectors (for example at 0°, 120° and 240°) to completely determine the sphere, cylinder and cylinder axis for the eye. It is possible to use more than three images to improve the measurement.

In order to increase measuring range, LEDs of increasing eccentricity may be used for each sector. For example, if the LED of least eccentricity for the first sector leads to saturation of the intensity gradient of the pupil, then the image corresponding to the LED of immediately higher eccentricity is used and so on until saturation is no longer observed. The intensity gradient in the pupil is considered to be saturated when the latter possesses zones in which the intensity, while being high, varies almost not at all (zone at the edge of the pupil).

The ametropia A1 for the sector i in question is then given by a function Fi that depends on the diameter of the pupil, the gradient and the eccentricity:

$$Ai = Fi(\text{Diam}, \text{Gradient}, \text{Ec}).$$

This function Fi is obtained by prior calibration of the apparatus or by calculation (see "Light-intensity distribution in eccentric photorefraction crescents", Kussel J. Opt. Soc. Am. A/Vol. 15, No. 6 (June 1998).

Step 3: Measurement in Another Posture and/or Another Visual Attitude

This time, the wearer is asked to look at a second target at a near-vision distance (see FIG. 2b). For this purpose, the target projected onto the ceiling by the source 13 is turned off and the wearer looks at the pattern screen-printed on the mirror 23.

It is normally not necessary at this stage to readjust the position and orientation of the case 6.

At this stage, the optician may ask the wearer to pivot his head in order to ensure that he adopts a suitable cephalic posture. For example, the wearer may be asked to raise his head while focusing on the screen-printed target until the point when his pupils are located at the lower edge of the frame, this location corresponding to a near-vision vision zone of a progressive glass.

Alternatively, the pantoscopic angle measured via the reference marks on the clip may be used to control the cephalic posture of the wearer or make him adopt a cephalic given posture, for example in order to make him adopt a cephalic posture in which his gaze is lowered by 30° relative to his far-vision posture.

In this case, the angle of rotation of the head between the first (far-vision) posture and the second (near-vision) posture is for example displayed on the screen 5 in order to help the optician ensure that an appropriate posture is adopted.

It may also be checked that the wearer is indeed looking at the screen-printed target by verifying that his gaze converges on the target, for example by measuring the relative positions of the pupils and corneal reflections.

All of these measurements (step 1 and step 2) may be carried out continuously and refraction may be measured for a continuous set of cephalic postures in each of the steps. From this set of measurements, the refraction measured at the points of intersection of the gaze and the plane of the frame may be displayed on an image representing the frame for the right eye and left eye.

Figure 6:
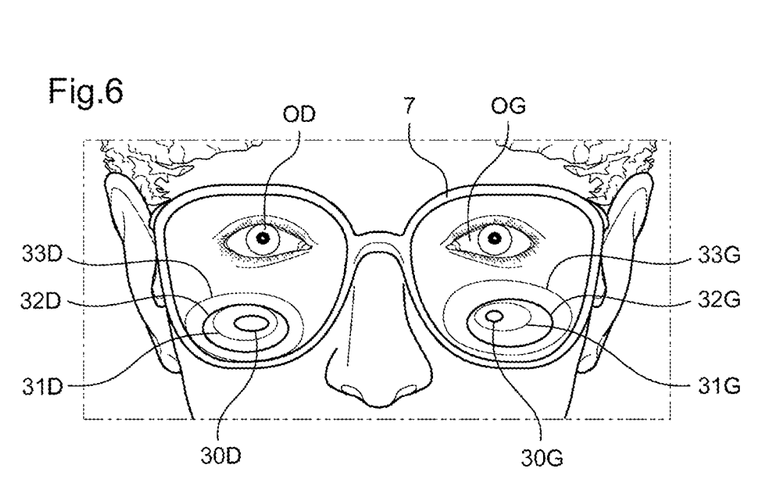
FIG. 6 schematically illustrates an image of a wearer of a pair of spectacles on which a map of the ocular refraction parameters measured under various vision and/or posture conditions has been drawn.

By way of illustrative example, FIG. 6 shows an image of a map of the refractions projected onto the plane of the frame. More precisely, FIG. 6 schematically illustrates an image of a wearer of a pair of spectacles on which a map has been drawn of ocular refraction parameters measured under various vision conditions and projected onto the plane of the correcting lenses. The curves 30G, 31G, 32G, 33G, 30D, 31D, 32D, 33D show examples of isosphere curves for near vision, in steps of 0.125 diopters between two adjacent curves, each curve being centered on the point of intersection of the gaze of each eye with the plane of the frame.

In addition, the refraction measurements may be made more precise by using the clip 8. Specifically, photorefraction is generally carried out without a precise measurement of distance, which leads to imprecise refraction measurements. Since the parameters of the clip are known, it is thus possible, using calibration or gauging procedures, to work out the precise distance between the device and the wearer, and to measure precisely pupil diameter and the distance between the pupil of an eye and the video camera. These two parameters are very important for the precision of the measurement. Specifically, the intensity gradient is proportional to the square of pupil diameter. An imprecise measurement of pupil diameter therefore generates a substantial error in the refraction measurement.

Frames equipped with corrective lenses (pre-fitted or trial lens) in order to correct at least partially the far-vision ametropia of the wearer may also be used. This makes it possible for the wearer to see relatively clearly in steps 2 and 3. The use of glasses of non-zero power during the measurement also makes it possible to limit the measuring range of the device and thus promote measurement precision. In this case, in practice, care is taken to ensure that reflections from the surfaces of the glasses do not superpose on the pupils of the eyes.

In addition, the measurement is corrected to take into account the loss of light related to reflections from the surfaces (about 4% per surface, out and back) and the power of the glass is deduced from the measurement.

Step Four (Optional) Measurement of PD/H/EGD/CRE

It is possible, in step 2 or step 3, to measure far-vision and near-vision pupillary distances. To do this, the reference marks 18, 28, 38 on the clip 8, the corneal reflections or the pupillary circle and the outline of the frame 7, which is imaged under infrared illumination, are all used, the reference marks 8, 28, 38 on the clip 8 being used to scale the image.

Infrared illumination has the advantage of generating an image of the pupils having a very good contrast and of not blinding the wearer.

Pupillary diameter or pupillary half-diameter is measured by measuring the center of the pupils (or corneal reflections) and by determining the center of the frame.

Heights (H) are measured by measuring the distance between the centers of the pupils and the right and left lower edges of the frame 7. Since head position has a substantial impact on the measurement of height, a two-step measurement may be envisioned in order to improve the precision of this measurement. In this case, a measurement is carried out in a natural posture (the wearer looking straight ahead) and then a second measurement is carried out, this second measurement being step 2 or step 3. The device is in this case equipped with an inclinometer in order to correct for posture.

Eye/glass distance (EGD) is measured by analyzing disparities between the two natural postures in steps 2 or 3.

The advantages of the method for measuring refraction of the invention are as follows:
- refraction measurements are obtained for varying cephalic postures;
- cephalic postures corresponding to natural postures are first measured and then refraction measurements are carried out in these measured postures;
- by controlling cephalic posture, the axis of the gaze remaining fixed and centered on the measurement axis, the gaze may be lowered by any amount relative to the head, thereby advantageously allowing an almost continuous measurement of refraction variation to be measured as a function of the lowering of the gaze relative to the head. Since the axis of the gaze remains fixed and inclined relative to the horizontal, the wearer may freely modify how much his gaze is lowered relative to his head simply by lowering or raising his head; and
- it is possible simultaneously to measure pupillary distances for various vision distances, and fitting parameters such as height/pantoscopic angle/EGD (if a clip is used), thereby allowing the number and length of the measurements required to produce a personalized glass to be limited.

The invention claimed is:

1. A binocular device for measuring at least one objective ocular refraction characteristic of a subject for a plurality of vision distances, comprising:
   an optical system for generating a focus of variable proximity, able to generate selectively a first target having a first proximity value P1 and at least one second target having a second proximity value P2, said first target and said second target being centered on one and the same focus optical axis;
   at least one light source able to generate at least one illuminating beam in the direction of the two eyes of the subject;
   an image-capturing apparatus, said apparatus having a measurement optical axis aligned with a gaze axis of the subject, the angle between the measurement optical axis and the focus optical axis being smaller than 10 degrees, said apparatus being suitable for receiving an ocular refraction beam by refraction of the at least one illuminating beam in the eyes of the subject, the image-capturing apparatus being suitable for capturing a first ocular refraction image of the two eyes when the first target of proximity P1 is activated and at least one second ocular refraction image of the two eyes when the second target of proximity P2 is activated as a function of lowering of the gaze relative to the head of the subject; and
   a processor suitable for receiving the first ocular refraction image and the second ocular refraction image in order to deduce therefrom a measurement of at least one objective ocular refraction characteristic of the two eyes of the subject depending on the first proximity value P1 and the second proximity value P2,
   a case holding the focus-generating optical system, the at least one light source and the image-capturing apparatus,
   the focus optical axis being inclined at an angle alpha to the horizontal, the angle alpha being comprised between +5 degrees and +85 degrees when the case is placed on a horizontal surface, and
   the image-capturing apparatus and the processor being suitable for measuring pupillary distances for the first proximity value P1 and for the second proximity value P2 and/or at least one fitting parameter among height, pantoscopic angle, eye/glass distance and the position of the center of rotation of the eye.

2. The measuring device as claimed in claim 1, further comprising:
   means for moving and/or orienting the focus optical axis so as to align the measurement optical axis with the axis of the gaze of the subject.

3. The measuring device as claimed in claim 1, further comprising:
   means for measuring the distance between said device and the head of the subject, said means for measuring distance being chosen from: a telemeter, an image-processing system based on image quality, an image-processing system based on the measurement of reference marks mounted on a clip fastened to a frame, a gauging system or a system for measuring distance by ultrasound.

4. The measuring device as claimed in claim 1, wherein the at least one light source comprises at least one infrared source and in which the image-capturing apparatus is able to capture images in the infrared.

5. The measuring device as claimed in claim 1, further comprising:
   an optical beam splitter placed on the optical path between the subject and the at least one source, the image-capturing apparatus, the optical beam splitter being able to combine the illuminating beam and the first target or the second target on the focus optical axis in the direction of the eyes of the subject, said beam splitter being able to direct the ocular refraction beam toward the image-capturing apparatus on the measurement optical axis.

6. The measuring device as claimed in claim 5, wherein the optical beam splitter comprises a dichroic mirror able to transmit the infrared illuminating beam and reflect the target beam.

7. The measuring device as claimed in claim 1, wherein the measurement optical axis and the focus optical axis are coincident.

8. The measuring device as claimed in claim 1, wherein the image-capturing apparatus is suitable for forming an image of the face of the subject on an object field having a diameter of at least 50 mm.

9. The measuring device as claimed in claim 2, further comprising:
   means for measuring the distance between said device and the head of the subject, said means for measuring distance being chosen from: a telemeter, an image-processing system based on image quality, an image-processing system based on the measurement of reference marks mounted on a clip fastened to a frame, a gauging system or a system for measuring distance by ultrasound.

10. The measuring device as claimed in claim 2, wherein the at least one light source comprises at least one infrared source and wherein the image-capturing apparatus is able to capture images in the infrared.

11. The measuring device as claimed in claim 3, wherein the at least one light source comprises at least one infrared source and wherein the image-capturing apparatus is able to capture images in the infrared.

12. The measuring device as claimed in claim 2, further comprising:
an optical beam splitter placed on the optical path between the subject and the at least one source, the image-capturing apparatus, the optical beam splitter being able to combine the illuminating beam and the first target or the second target on the focus optical axis in the direction of the eyes of the subject, said beam splitter being able to direct the ocular refraction beam toward the image-capturing apparatus on the measurement optical axis.

13. The measuring device as claimed in claim 3, further comprising:
an optical beam splitter placed on the optical path between the subject and the at least one source, the image-capturing apparatus, the optical beam splitter being able to combine the illuminating beam and the first target or the second target on the focus optical axis in the direction of the eyes of the subject, said beam splitter being able to direct the ocular refraction beam toward the image-capturing apparatus on the measurement optical axis.

14. The measuring device as claimed in claim 4, further comprising:
an optical beam splitter placed on the optical path between the subject and the at least one source, the image-capturing apparatus, the optical beam splitter being able to combine the illuminating beam and the first target or the second target on the focus optical axis in the direction of the eyes of the subject, said beam splitter being able to direct the ocular refraction beam toward the image-capturing apparatus on the measurement optical axis.

15. The measuring device as claimed in claim 4, wherein the image-capturing apparatus is suitable for forming an image of the face of the subject on an object field having a diameter of at least 50 mm.

16. The measuring device as claimed in claim 5, wherein the image-capturing apparatus is suitable for forming an image of the face of the subject on an object field having a diameter of at least 50 mm.

17. The measuring device as claimed in claim 6, wherein the image-capturing apparatus is suitable for forming an image of the face of the subject on an object field having a diameter of at least 50 mm.

* * * * *